(12) United States Patent
Soon-Shiong (10) Patent No.: US 11,564,944 B2
(45) Date of Patent: *Jan. 31, 2023

(54) FRACTAL COMBINATION THERAPY

(71) Applicant: NANT HOLDINGS IP, LLC, Culver City, CA (US)

(72) Inventor: Patrick Soon-Shiong, Culver City, CA (US)

(73) Assignee: Nant Holdings IP, LLC, Culver City, CA (US)

( * ) Notice: Subject to any disclaimer, the term of this patent is extended or adjusted under 35 U.S.C. 154(b) by 160 days.

This patent is subject to a terminal disclaimer.

(21) Appl. No.: 16/462,733

(22) PCT Filed: Nov. 20, 2017

(86) PCT No.: PCT/US2017/062490
§ 371 (c)(1),
(2) Date: May 21, 2019

(87) PCT Pub. No.: WO2018/094309
PCT Pub. Date: May 24, 2018

(65) Prior Publication Data
US 2019/0365811 A1    Dec. 5, 2019

Related U.S. Application Data

(60) Provisional application No. 62/424,990, filed on Nov. 21, 2016.

(51) Int. Cl.
| | | |
|---|---|---|
| *A61K 35/17* | (2015.01) | |
| *A61K 47/64* | (2017.01) | |
| *A61K 35/761* | (2015.01) | |
| *A61K 39/00* | (2006.01) | |
| *C07K 14/52* | (2006.01) | |
| *C07K 14/74* | (2006.01) | |
| *C12N 5/0783* | (2010.01) | |

(52) U.S. Cl.
CPC ............ *A61K 35/17* (2013.01); *A61K 35/761* (2013.01); *A61K 39/0011* (2013.01); *A61K 47/642* (2017.08); *C07K 14/521* (2013.01); *C07K 14/70539* (2013.01); *C12N 5/0638* (2013.01); *A61K 2039/5154* (2013.01); *A61K 2039/5156* (2013.01); *C07K 2319/33* (2013.01)

(58) Field of Classification Search
None
See application file for complete search history.

(56) References Cited

U.S. PATENT DOCUMENTS

| | | |
|---|---|---|
| 7,758,891 B2 | 7/2010 | Desai et al. |
| 7,771,751 B2 | 8/2010 | Desai et al. |
| 7,780,984 B2 | 8/2010 | Desai et al. |
| 7,981,445 B2 | 7/2011 | De et al. |
| 8,034,375 B2 | 10/2011 | Desai et al. |
| 8,795,672 B2 | 8/2014 | Epstein et al. |
| 2003/0171551 A1 | 9/2003 | Rosenblatt et al. |
| 2008/0166367 A1* | 7/2008 | Panicali ................. A61P 35/00 424/185.1 |
| 2011/0027310 A1* | 2/2011 | Medin ................ C07K 14/5434 435/325 |
| 2011/0044953 A1* | 2/2011 | Allison .............. C07K 16/2818 424/93.7 |
| 2012/0059670 A1 | 3/2012 | Sanborn et al. |
| 2012/0066001 A1 | 3/2012 | Sanborn et al. |
| 2015/0258186 A1* | 9/2015 | Florkiewicz ........... C07K 14/82 424/133.1 |
| 2016/0009784 A1 | 1/2016 | Campana et al. |
| 2016/0237137 A1 | 8/2016 | Webb et al. |
| 2017/0247453 A1 | 8/2017 | Dimitrov et al. |
| 2017/0312351 A1* | 11/2017 | Niazi ...................... C07K 7/06 |
| 2018/0363005 A1* | 12/2018 | Soon-Shiong ..... A61K 38/2046 |

FOREIGN PATENT DOCUMENTS

| | | |
|---|---|---|
| CA | 3 044 424 A1 | 5/2018 |
| WO | 2000/063395 A1 | 10/2000 |
| WO | 2002036769 A2 | 5/2002 |
| WO | 2005/026370 A2 | 3/2005 |
| WO | 2005/026370 A3 | 6/2005 |
| WO | 2011/139345 A3 | 3/2012 |
| WO | 2013/062505 A1 | 5/2013 |
| WO | 2016/172722 A1 | 10/2016 |
| WO | 2017/035392 A1 | 3/2017 |
| WO | 2017/100338 A1 | 6/2017 |

OTHER PUBLICATIONS

Gallo et al., 2005. Gene Ther. vol. 12: S84-S91.*
Scott et al., 2012, Nature, vol. 12: 278-287.*
Kornbluth, 2013, J. Immunother. Cane. vol. 1(Suppl1):P20.*
Macdonald, 2014, J. Immunol. vol. 193: 5056-5064.*
Partial Supplementary European Search Report received for European Patent Application Serial No. EP17871290.7, dated Jul. 2, 2020, 15 pages.
Examination Report No. 1 received for Australian Patent Application Serial No. 2017362730 dated Oct. 8, 2020, 5 pages.
Extended European Search Report received for European Patent Application Serial No. 17871290.7 dated Oct. 7, 2020, 13 pages.

(Continued)

*Primary Examiner* — Amy E Juedes (74) *Attorney, Agent, or Firm* — Martin Fessenmaier; Umberg Zipser LLP (57) ABSTRACT

Contemplated compositions and methods generate a durable immune synapse and so lead to activated T-cells and memory T-cell formation by use of selected co-stimulatory receptors and their ligands in conjunction with selected neoepitopes. Moreover, immune competent cells are attracted into a tumor microenvironment after activation of the T-cells using hybrid or chimeric binding proteins that comprise a chemokine portion and that target components of necrotic cells.

6 Claims, 1 Drawing Sheet

(56) References Cited

OTHER PUBLICATIONS

Pento Joseph Thomas, "Monoclonal Antibodies for the Treatment of Cancer", Anticancer Research, 2017, vol. 37, No. 11, pp. 5935-5939.

Lundegaard et al., "NetMHC-3 0: accurate web accessible predictions of human, mouse and monkey MHC class I affinities for peptides of length 8-11", Nucleic Acids Research,May 7, 2008, vol. 36, No. 2, pp. W509-W512.

Zhang et al., "Machine learning competition in immunology—Prediction of HLA class I binding peptides", Journal of Immunological Methods, 2011, vol. 374, pp. 1-4.

Amalfitano et al., "Production and Characterization of Improved Adenovirus Vectors with the E1, E2b, and E3 Genes Deleted", Journal of Virology, 1998, vol. 72, No. 2, pp. 926-933.

Niazi et al., "Activation of human CD4+T cells by targeting MHC class II epitopes to endosomal compartments using human CD1 tail sequences", Immunology, 2007, vol. 122, No. 4, pp. 522-531.

Wang et al., "Fusion of chemotactic peptide to a single-chain bi-specific antibody (scBsAb) potentiates its cytotoxicity to target tumour cells", Biotechnology and Applied Biochemistry, 2006, vol. 45, No. 3, pp. 147-154.

International Search Report and Written Opinion received for PCT Application Serial No. PCT/US2017/062490, dated Oct. 31, 2018, 17 pages.

Cameron et al., "Artificial antigen presenting cells for use in adoptive immunotherapy", The Cancer Journal, 2010, vol. 16, No. 4, pp. 374-381.

International Preliminary Report on Patentability received for PCT Application Serial No. PCT/US2017/062490, dated May 31, 2019, 14 pages.

Office Action received for Canadian Application Serial No. CA3044424, dated Jun. 4, 2020, 6 pages.

Carter et al., "No patient left behind: The promise of immune priming with epigenetic agents", Oncoimmunology 2017, vol. 6, No. 10, 14 pages.

Cheuk et al., "Role of 4-1BB:4-1BB ligand in cancer immunotherapy", Cancer Gene Therapy (2004) 11, Dec. 12, 2003, pp. 215-226.

Tureci et al., "Targeting the Heterogeneity of Cancer with Individualized Neoepitope Vaccines", CCR Focus, Nov. 13, 2017, 13 pages.

Hartmann et al., "Clinical development of CAR T cells—challenges and opportunities in translating innovative treatment concepts", EMBO Molecular Medicine, vol. 9, No. 9, Aug. 1, 2017, pp. 1183-1197.

Christian Pascal Hess, "Targeted delivery of immunomodulatory proteins: evaluation of novel antibody-chemokine and antibody-cytokine fusion proteins for cancer therapy", Diss. ETH No. 22338, ETH Zurich, 203 pages.

Brennick et al., "Neoepitopes as cancer immunotherapy targets: key challenges and opportunities", future science group, Immunotherapy (2017) 9(4), pp. 361-371.

Chen et al., "Molecular mechanisms of T cell co-stimulation and co-inhibition", htttps://www.ncbi.nlm.nih.gov/pmc/articles/PMC3786574, Mar. 8, 2013, pp. 1-32.

Turnis et al., "Enhancement of dendritic cells as vaccines for cancer", https://www.ncbi.nlm.nih.gov/pmc/articles/PMC3433954, Sep. 5, 2012, pp. 1-24.

Hess et al., "Evaluation of Antibody-Chemokine Fusion Proteins for Tumor-Targeting Applications ", Exp Biol Med (Maywood), Jul. 2014, vol. 239 No. 7, pp. 842-852.

Office Action received for Canadian Patent Aplication Serial No. 3044424 dated Mar. 9, 2021, 6 pages.

Na et al., "TAGLN2 regulates T cell activation by stabilizing the actin cytoskeleton at the immunological synapse", The Journal of Cell Biology, 2015, vol. 209, No. 1, pp. 143-162.

Notice of acceptance received for Australian Patent Application Serial No. 2017362730 dated Mar. 29, 2021, 3 pages.

Examination report No. 2 received for Australian Patent Application Serial No. 2017362730 dated Jan. 25, 2021, 4 pages.

Turnis et al., "Enhancement of dendritic cells as vaccines for cancer", Immunotherapy,2010, vol. 2, No. 6, pp. 847-862.

Office Action received for Canadian Patent Application Serial No. 3,044,424 dated Feb. 11, 2022, 3 pages.

* cited by examiner

FRACTAL COMBINATION THERAPY

This application claims priority to our U.S. provisional application with the Ser. No. 62/424,990, filed Nov. 21, 2016.

FIELD OF THE INVENTION

The field of the invention is cancer therapy, especially as it relates to cancer therapy with multiple treatment modalities.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Tumor immune therapy has recently gained momentum, at least in part due to successful treatments using one or more therapeutic entities, and especially checkpoint inhibitors (see e.g., *Anticancer Res.* 2017 November; 37(11): 5935-5939). Other therapeutic interventions have also shown promise using epigenetic stimulation (e.g., *Oncoimmunology* 2017 Aug. 30; 6(10):e1315486), and neoepitope based treatment is now considered one of the most promising therapeutic options (e.g., *Immunotherapy* 2017 March; 9(4):361-371; *Clin Cancer Res.* 2016 Apr. 15; 22(8):1885-96). Likewise, the use of genetically engineered NK and T cells with chimeric antigen receptors has found remarkable responses in at least a subset of patients (see e.g., *EMBO Mol Med.* 2017 September; 9(9):1183-1197). However, while such treatments at least conceptually should stimulate an immune response, tumor complexity and the intricate timing and molecular requirements for an effective immune response often prevent a desired therapeutic effect. For example, where a tumor antigen is presented by an antigen presenting cell, strength and duration of the interaction between the antigen presenting cell and a naïve T cell at the immune synapse typically determine whether the T cell will become an anergic T cell or a cytotoxic T cell, and as such whether or not the tumor antigen will be tolerated or eradicated. Moreover, even if a T cell is induced to become a cytotoxic T cell, other immune competent cells (and especially NK cells and macrophages) are often required to produce a clinically meaningful response. Unfortunately, presence and activity of such cells is often insufficient, typically due to the particular defense mechanisms of a tumor that are often found in the tumor microenvironment.

Thus, mechanistic considerations alone focusing on one or another aspect of an immune response will generally not result in an effective immune response to a tumor as a therapeutically effective immune response depends on presence, sequence, and timing of various components in the tumor. Consequently, there remains a need for improved compositions and methods to treat cancer using immune therapy.

SUMMARY OF THE INVENTION

The inventive subject matter is generally directed to various compositions and methods in which multiple immune therapy treatment modalities are orchestrated to target tumor cells. Most preferably, various compositions and methods are employed to enhance or ensure activation of T cells and formation of memory T cells to so help produce a therapeutically effective immune response against a tumor. These benefits are achieved, inter alia, by enhanced formation of a stimulatory immune synapse and concomitant or subsequent recruitment of immune competent cells. Where desired, an immune response may be further promoted using inhibition of immune suppression.

In one aspect of the inventive subject matter, the inventors contemplate a method of activating T-cells to generate memory T-cells, and preferred methods include a step of genetically modifying an antigen presenting cell to (a) express a co-stimulatory receptor and its ligand, wherein the receptor and the ligand are optionally coupled together via a linker or form a chimeric protein; and (b) express at least one of an MHC-I polytope and an MHC-II polytope. In a further step, the genetically modified antigen presenting cell is contacted with a naïve T-cell, wherein the receptor and the ligand are expressed in the genetically modified antigen presenting cell in sufficient quantities to form an immune synapse that activates the T-cell. Where desired, the receptor and the ligand are coupled together via a linker or form a chimeric protein.

In further preferred aspects of the inventive subject matter, the co-stimulatory receptor is OX-40 and the ligand is OX-40L, and/or the co-stimulatory receptor is 4-1BB and the ligand is 4-1BBL. Moreover, it is typically preferred that MHC-I and MHC-II polytopes are expressed, and/or that at least one of the MHC-I and MHC-II polytopes comprise a tumor and patient specific neoepitope (which may or may not be the same). In yet further preferred aspects, the step of genetically modifying the antigen presenting cell comprises a step of infecting of the antigen presenting cell with a recombinant virus that comprises a sequence encoding the co-stimulatory receptor, the ligand, the MHC-I polytope, and the MHC-II polytope. Thus, the step of infecting may be performed in vivo or in vitro. In addition, it should be appreciated that the recombinant virus may also include a sequence encoding a checkpoint inhibitor and/or an immune stimulatory cytokine or cytokine analog.

Therefore, the inventor also contemplates a method of treating a cancer in a patient. Such method will typically include a step of administering a recombinant vaccine to the patient, wherein the recombinant vaccine comprises a recombinant nucleic acid sequence that encodes (a) a co-stimulatory receptor and its ligand, wherein the receptor and the ligand are optionally coupled together via a linker or form a chimeric protein; and (b) at least one of an MHC-I polytope and an MHC-II polytope. Most typically, the recombinant nucleic acid sequence is configured to allow co-expression of the at least one of the MHC-I polytope and the MHC-II polytope, the receptor, and the ligand in an antigen presenting cell in sufficient quantities to form an immune synapse that activates the T-cell. As noted above, it is generally preferred that the co-stimulatory receptor is OX-40 and the ligand is OX-40L, and/or that the co-stimulatory receptor is 4-1BB and the ligand is 4-1BBL.

In further contemplated aspects, such methods may further comprise a step of reducing immune suppression in a tumor microenvironment in the patient before the step of administering the recombinant vaccine, most typically (but not necessarily) via delivery of a pharmaceutical agent across the neovasculature of the tumor microenvironment, for example via transcytosis or use of a permeability enhancing peptide. Additionally, contemplated treatment methods may also include a step of attracting immune competent cells to the cancer by targeting necrotic tumor cells within a microenvironment using a fusion protein comprising an antibody portion that binds to a component of a necrotic cell and a chemokine portion. Where desired, a further step of administering to the patient an immune stimulatory chimeric protein comprising an Fc portion and an IL-15 receptor portion may be implemented.

Consequently, the inventor also contemplates a fusion protein (and nucleic acids encoding same) for activating a T-cell that comprises a co-stimulatory receptor and its ligand, wherein the receptor and the ligand are coupled together via a linker. Most typically, the linker is a peptide, a polymer, or a covalent bond, and the co-stimulatory receptor is OX-40 while the ligand is OX-40L and/or the co-stimulatory receptor is 4-1BB while the ligand is 4-1BB L.

Viewed from a different perspective, the inventor also contemplates a recombinant nucleic acid that includes a nucleic acid sequence that encodes: (a) a co-stimulatory receptor and its ligand, wherein the receptor and the ligand are optionally coupled together via a linker or form a chimeric protein; and (b) at least one of an MHC-I polytope and an MHC-II polytope. In preferred aspects, the recombinant nucleic acid sequence is configured to allow co-expression of the at least one of the MHC-I polytope and the MHC-II polytope, the receptor, and the ligand.

In preferred aspects, the co-stimulatory receptor is OX-40 and the ligand is OX-40L, and/or the co-stimulatory receptor is 4-1BB and the ligand is 4-1BB L. Additionally, the nucleic acid sequence may further encode a checkpoint inhibitor. Where the nucleic acid sequence encodes the MHC-I polytope and the MHC-II polytope it is contemplated that at least one of the polytopes comprise a patient and tumor specific neoepitope. Advantageously, the nucleic acid sequence is part of a viral genome, and most preferably the viral genome is an adenoviral genome.

Thus, in yet another aspect of the inventive subject matter, the inventor also contemplates an antigen presenting cell (e.g., dendritic cell) expressing the fusion protein presented herein, wherein the antigen presenting cell also presents a neoepitope, a cancer-associated antigen, or a cancer-specific antigen on at least one of MHC-I and MHC-II. Preferably, the antigen presenting cell is genetically engineered using an adenovirus that has a nucleic acid which encodes for the fusion protein, and/or the neoepitope is patient-specific or cancer specific. As noted already, it is generally preferred that the co-stimulatory receptor is OX-40 and the ligand is OX-40L, and/or that the co-stimulatory receptor is 4-1BB and the ligand is 4-1BB L.

In view of the above, it should therefore also be appreciated that the inventor contemplates a method of treating a cancer in a patient that includes a one step of generating an immune stimulus by administering a recombinant vaccine to the patient, wherein the recombinant vaccine (e.g., recombinant adenovirus) comprises a recombinant nucleic acid sequence that encodes (a) a co-stimulatory receptor and its ligand, wherein the receptor and the ligand are optionally coupled together via a linker or form a chimeric protein; and (b) at least one of an MHC-I polytope and an MHC-II polytope. Most preferably, the recombinant nucleic acid sequence is configured to allow co-expression of the at least one of the MHC-I polytope and the MHC-II polytope, the receptor, and the ligand in an antigen presenting cell in sufficient quantities to form an immune synapse that activates the T-cell. In another step, immune competent cells (e.g., NK cells, dendritic cells, or T-cells) are attracted to a tumor after generating the immune stimulus by administering an effective amount of a fusion protein comprising an antibody portion and a chemokine portion, wherein the antibody portion binds to a component of a necrotic cell (e.g., nucleolin, a histone protein, or ssDNA). Where desired, contemplated methods may also include a step of administering PEP or IL2 in an amount effective to increase delivery of a therapeutic agent to a tumor microenvironment.

In some aspects, the step of administering the fusion protein may be performed concurrently with or after a step of treating a tumor microenvironment to reduce immune suppression, while in other aspects contemplated treatment methods may further include a step of administering a second fusion protein comprising an Fc portion and an immune stimulatory portion. Most typically, the chemokine portion comprises an inflammatory chemokine or portion thereof, or the chemokine portion comprises one or more of LEC, CCL1, CCL2, CCL3, CCL4, CCL5, CCL11, CCL17, CCL22, CXCL-8, CXCL-10, and CXCL-14. Moreover, it is contemplated that the antibody portion comprises one or more of a humanized antibody portion, a Fab, a scFv, a F(ab)$_2$, and a Fab', and that the fusion protein is a chimeric protein comprising the antibody portion and the chemokine portion.

Various objects, features, aspects and advantages of the inventive subject matter will become more apparent from the following detailed description of preferred embodiments, along with the accompanying drawing.

DETAILED DESCRIPTION

The inventive subject matter is directed toward various compositions and methods which allow for orchestrated interactions of molecules at the immune synapse to promote a strong and durable interaction between an antigen presenting cell and naïve T cells, and various immune competent cells to augment an adaptive immune response. Using the compositions and methods presented herein, the inventors therefore contemplate that not only a therapeutically effective immune response, but also immune memory can be generated.

More particularly, the inventors contemplate that such therapeutically effective immune response requires a multitude of factors and timed events, that can be delivered/generated using various recombinant adenoviral (or yeast and/or bacterial) vaccine compositions, preferably in conjunction with other therapeutic entities as further discussed below. Table 1 exemplarily lists some of the factors/timed events, along with selected mechanistic considerations. Of course, it should be appreciated that the exemplary compounds and events are by no means exhaustive, and that numerous alternative and/or additional compounds and events may be suitable.

As is shown in Table 1, access to the tumor microenvironment to provide targeted drug delivery can be achieved using drug conjugates with albumin, which is preferentially taken up in to a tumor via gp60 mediated transcytosis at the tumor neovasculature. For example, taxane-type compounds can be coupled to albumin, which is then delivered to the tumor. In a less specific approach, permeability enhancing peptides (e.g., from PEP portion of IL2) or NO can be given to systemically render the vasculature more 'leaky' and so allow for delivery of drugs to the tumor. Such drugs and compositions may be used to deliver chemotherapeutic agents to a tumor, which may increase expression of stress signals (e.g., MICA NKG2D) that can then serve as a trigger for NK cells for cytotoxic action. In especially preferred aspects, as is discussed in more detail below, NK cells can be specifically attracted to the tumor microenvironment using chemokines that are more preferably coupled to one or more antibodies that specifically bind to a component of a tumor, and most preferably a necrotic tumor cell.

Where vaccine compositions are employed, it is particularly preferred that the vaccine is a recombinant bacterial, yeast, or adenoviral vaccine that delivers a tumor associated antigen or a patient and tumor specific neoepitope, most preferably configured for specific presentation by the MHC I and/or MHC II complex as is also discussed in more detail below. Most typically, the vaccine composition will also include a nucleic acid encoding co-stimulatory molecules B7-1 (CD80) and//or B7-2 (CD86). As will be readily appreciated, co-expression of co-stimulatory factors B7-1 and B7-2 will increase molecular interactions between the antigen presenting cells and T cells, thus strengthening cellular interactions. For further enhancement and maintenance of the immune synapse, it is contemplated that the vaccine composition (and particularly where the vaccine is a viral vaccine) also provides a nucleic acid that encodes for further protein factors that strengthen and/or complete a stimulatory immune synapse, leading to T cell activation. For example, especially suitable protein factors include Ox40, Ox40 ligand, 4-1BB, 4-1BB ligand, GitR, GitR ligand, LTLA4, CTLA-4, B7.1, B7.2, CD154, and CD40 as is further discussed in more detail below.

In addition, it should be recognized that an immune response also requires interaction with or modulation of other cellular components of the immune system, and especially suppression of suppressor cells, inhibition of existing suppressor cells, and activation of activators. For example, suppressor cells can be suppressed using various cytokines, and especially IL-2 and IL-15 (and in some cases IL-8). Likewise, suppressor cells can be inhibited using various chemotherapeutic drugs, such as cyclophosphamide, paclitaxel, nano-particulate albumin plus cisplatinum or oxaliplatinum. On the other hand, activators that can be stimulated via immune stimulatory cytokines (e.g., IL15, ALT-803, etc.) or interferons to upregulate STING pathway responses.

As noted above, the adaptive immune response can be further augmented by recruitment of one or more immune competent cells, and especially naïve T cells, and NK cells. Preferably, such recruitment is specific to the tumor microenvironment and can be effected by use of targeting antibody-chemokine hybrid proteins, and/or expressed of chemokines and/or antibody-chemokine hybrid proteins in a cell in or near the tumor microenvironment as is also further discussed in more detail below.

| Event | Process(es) | Cell(s) | Protein(s) | Other |
|---|---|---|---|---|
| Cross blood-vessel barrier to tumor microenvironment | (1) Activate protein transcytosis (2) Permeability of vasulature | Blood vessel cells | GP60 IL-2 IL-15 | NO, O2, PEP |
| Activate dendritic cell | Signal MHC restriction | Dendritic cell | Neoepitope or tumor antigen MHC1 MHC2 B7.1 B7.2 | |
| Create Activated T-cell | Synapse between dendritic cell and t-cell for appropriate duration | Dendritic cell T-cell Treg cells | Ox40 Ox40 ligand 4-1BB 4-1BB ligand GitR GitR ligand LTLA4 CTLA-4 B7.1 B7.2 CD154 CD40 | |
| | (1) Suppress suppressors | Dendritic cell T-cell Treg cells Macrophage inhibiting cells | IL-15 IL-2 IL-8 | SSU chemo |
| | (2) Activate activators. STING pathway | Dendritic cell T-cell Treg cells | Ox40 CD40 41DB GitR nfKb interferons | Chemo interferon stimulating gene tumor necrosis molecule |

-continued

| Event | Process(es) | Cell(s) | Protein(s) | Other |
|---|---|---|---|---|
| | (3) Inhibit suppressors | | PDLA-1<br>CKLA-4<br>GitR | Cyclophosphamide<br>Paclitaxel,<br>Cytoxan |
| Recruit immune competent cells to tumor microenvironment | | Dendritic cells<br>T cells<br>NK cells | INFs<br>Cp60<br>IL-2<br>IL-15<br>Histone proteins<br>Nucleolin 1<br>Chemokine<br>LEK<br>Chemoattractant | |
| | Recruit NK cells | NK cells | NKg2D<br>MICA<br>NKP30<br>NKP40<br>Adhesion proteins<br>GD40<br>CD69<br>CD16 | |

Therefore, it should be appreciated that cancer therapy can be targeted to maximize a tumor cell specific immune response and formation of memory T cells and NK cells while maintaining and augmenting a patients' antitumor adaptive and innate responses to cancers. To that end, the treatment methods and uses of specific compounds and compositions presented herein take advantage of recombinant vaccines that provide neoepitopes in their context with co-stimulatory molecules and further stimulating factors to form an effective immune synapse for generation of activated T cells, preferably along with immunomodulatory agents, checkpoint inhibitors, and/or fusion proteins to augment and stimulate the patient's adaptive and innate immune responses. In addition, contemplated compositions will also be effective in recruitment of immune competent cells to the tumor microenvironment preferably by use of fusion proteins that include a binding portion (e.g., to components of necrotic cells) and a chemokine portion. It should further be appreciated that preferred combinations will be targeted to mutational patterns specific to a patient, and as such off-target stimulation of an immune response is significantly reduced.

Most preferably, contemplated compounds and compositions are configured/administered to achieve a temporal spatial orchestration of a combination of immunotherapeutic effects to so immunomodulate the tumor microenvironment, activate the adaptive immune system, stimulate the innate immune system, induce immunogenic cell death (ICD), and/or to form memory T cells and memory NK cells. More specifically, the inventors contemplate that such approach will result in coordinated effects, and especially in generation of a durable immune synapse leading to activation of a T cell (as opposed to the generation of an anergic T cell), and to recruitment of immune competent cells to augment an adaptive immune response and attract an innate immune response.

Figure 1:
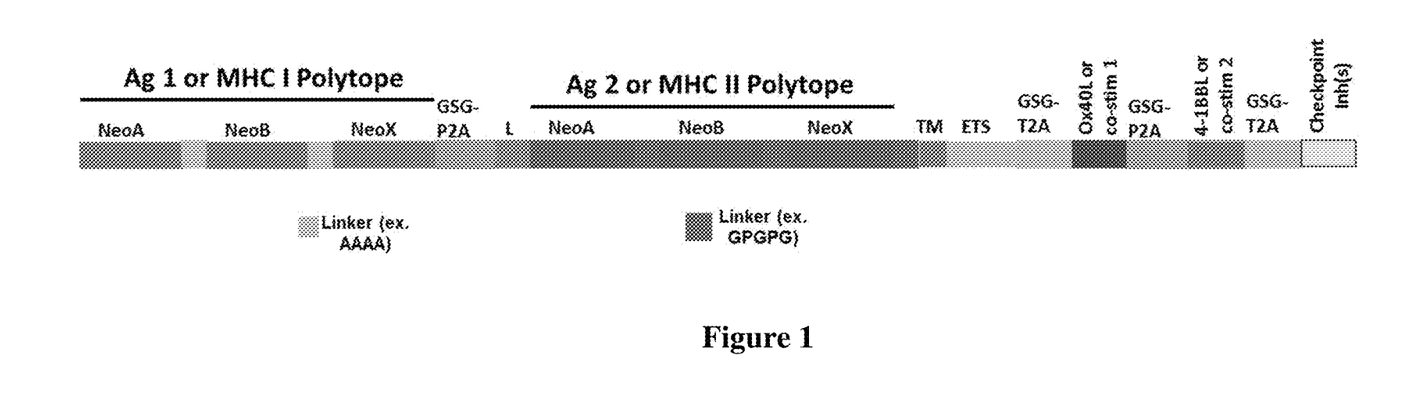
FIG. 1 is a schematic illustration of one exemplary recombinant nucleic acid according to the inventive subject matter.

For example, where an immune therapy for a tumor comprises a viral vaccine component (and especially a recombinant adenoviral vaccine), the recombinant virus may be constructed to include sequences encoding tumor and patient specific neoepitopes in addition to co-stimulatory molecules and one or more checkpoint inhibitors as is exemplarily depicted in FIG. 1. Here, multiple antigens and/or tumor neoepitopes for directed MHC I and MHC II presentation are encoded in form of a polytope in which the individual antigens and/or tumor neoepitopes (NeoA, NeoB . . . ) are separated by a peptide linker, and in which a self-cleaving 2A peptide is placed between the polytopes. Of course, it should be appreciated that the polytopes will include the appropriate addressing sequence elements to route the polytope to the respective MHC complexes. In addition to the polytopes, the construct also includes a sequence portion that encodes first and second co-stimulatory factors, and particularly OX40 ligand and 4-1BB ligand, again separated by a self-cleaving 2A peptide. As is also shown in FIG. 1, the recombinant sequence will also include a sequence portion encoding one or more checkpoint inhibitors (e.g., anti-PD1, anti-CTLA4, etc.), preferably in form of a scFv.

It should be particularly appreciated that such recombinant nucleic acid will not only deliver one or more neoepitopes to a dendritic (or other antigen presenting) cell but also provides OX40 ligand and/or 4-1BB ligand (and where desired further co-stimulatory molecules such as B7-1, B7-2, GitR ligand, CD153, CD40, and/or ICOS ligand, etc.) which are believed to be critical in the final steps for formation of an immune synapse that has stimulatory effect on a T cell. Furthermore, OX40/OX40 ligand interaction as well as 4-1BB/4-1BB ligand interaction is thought to facilitate long-term interaction between the T cell and the antigen presenting cell, as well as facilitate memory T cell and memory NK cell formation. Where the recombinant nucleic acid further includes one or more checkpoint inhibitors, inhibitory signals (from a T cell or tumor cell) can be prevented in the proper context of the neoepitopes and/or tumor antigens while stimulating signals are provided in the same proper context of the neoepitopes and/or tumor antigens.

Figure 2:
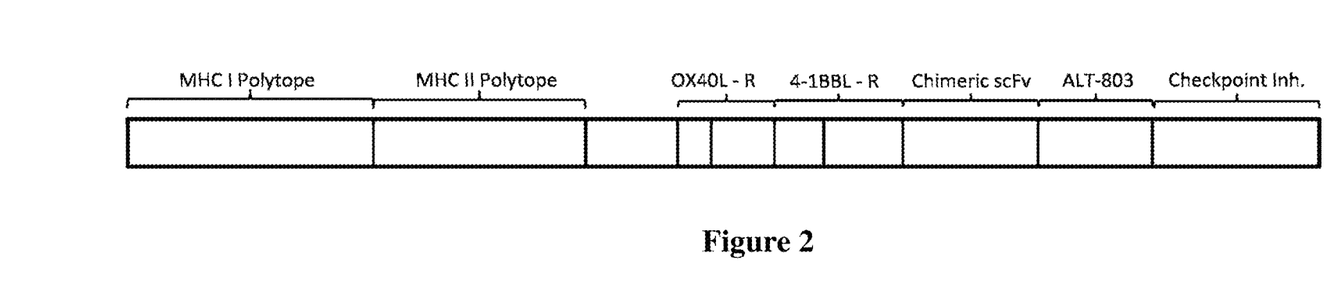
FIG. 2 is a schematic illustration of another exemplary recombinant nucleic acid according to the inventive subject matter.

Of course, it should be recognized that contemplated recombinant may further comprise one or more additional sequences encoding one or more proteins that further stimulate formation and maintenance of the immune synapse and/or attract immune competent cells to the tumor microenvironment as is schematically and exemplarily depicted in FIG. 2. Here, similar to the recombinant nucleic acid of FIG. 1, the recombinant nucleic acid (that is preferably part of a viral expression vector or viral genome) includes segments encoding multiple antigens and/or tumor neoepitopes for MHC I and MHC II, typically in the form of a polytope in which the individual antigens and/or tumor neoepitopes (NeoA, NeoB . . . ) are separated by a peptide linker, and in which a self-cleaving 2A peptide is placed between the polytopes.

As before, it should be appreciated that the polytopes will preferably include appropriate addressing sequence elements to route the polytope to the respective MHC complexes. In addition to the polytopes, suitable constructs will also include a sequence portion that encodes not only a co-stimulatory factor, but also the corresponding receptor for the co-stimulatory factor. For example, the recombinant nucleic acid may encode both the OX40 ligand and the corresponding OX40 receptor, and/or both the 4-1BB ligand and the corresponding 4-1BB receptor (with the sequences preferably separated by a self-cleaving 2A peptide). Optionally, as is further discussed in more detail below, the ligand and receptor may form a chimeric protein, typically by coupling the ligand to the receptor via a linker peptide. As is shown in FIG. 2, the recombinant sequence may further include a sequence portion encoding a chimeric molecule that has a targeting portion and a chemokine portion, wherein the targeting portion binds to a component of a necrotic cell (e.g., nucleolin, histone proteins, ssDNA, etc.). In addition, where desired, the recombinant sequence may further include a segment encoding one or more checkpoint inhibitors (e.g., anti-PD1, anti-CTLA4, etc.), preferably in form of a scFv.

Such viral vectors are deemed especially effective as the antigen/neoepitope presentation is effected in the context of OX40/OX40 ligand complex and/or a 4-1BB/4-1BB ligand complex. While not limiting to the inventive subject matter, the inventor especially contemplates that the OX40/OX40 ligand (chimeric) complex and/or a 4-1BB/4-1BB ligand (chimeric) complex have substantially increased activation effect upon formation of the immune synapse, likely due to conformational activation of the OX40 ligand and/or the 4-1BB ligand, and/or due to cooperative protein/protein interactions between OX40 and/or 4-1BB and other receptor proteins (part of the immune synapse) at the T cell.

Additionally, where the recombinant nucleic acid includes a chimeric molecule that has a targeting portion and a chemokine portion (with the targeting portion binding a component of a necrotic cell and the chemokine being a chemoattractant to T cells and NK cells), secretion of such chimeric protein will result in 'tagging' necrotic cells in the tumor microenvironment and concurrent recruitment of various immune competent cells, and particularly dendritic cells, NK cells, and naïve T cells. Thus, it should be appreciated that recombinant viruses as contemplated herein will provide an orchestrated assembly of components that are required for formation of an immune synapse and further components that enhance/augment T cell activation upon delivery of the recombinant components, all in context of the proper antigens/neoepitopes. Additionally, the immune therapy can be further enhanced by administration of various drugs to stimulate immune responses, such as immune stimulatory cytokines (and especially IL15 or ALT-803) and one or more cytotoxic drugs (preferably under a low-dose metronomic regimen) that stimulate a stress response in tumor cells. Such stress response will typically include overexpression of NKG2D, MICA, NKp30, and/or NKp40, all of which stimulate in turn NK cytotoxic cell killing.

With respect to construction of suitable recombinant nucleic acids, (adeno)viral vectors, and vaccines, it is contemplated that neoepitope-based immune therapy will employ targeting of expressed patient- and tumor specific neoepitopes towards processing and/or specific cell surface presentation or even secretion, and as noted above, that neoepitope-based therapy can still further be augmented using co-stimulatory molecules, checkpoint inhibition, immune stimulation via cytokines, and/or inhibitors of myeloid derived suppressor cells (MDCS), T-regulatory cells (Tregs), or M2 macrophages. Most preferably, such therapeutic entities will be expressed in vivo from a recombinant nucleic acid, and especially suitable recombinant nucleic acids include mRNA, DNA, plasmids, and particularly viral nucleic acids. Where a viral nucleic acid is used, it is especially preferred that the nucleic acid is delivered via infection of the patient or patient cells by the virus.

Viewed from a different perspective, it should be appreciated that the compositions and methods presented herein will include one or more neoepitopes that are specific to the patient and the tumor in the patient to allow for targeted treatment. Moreover, such treatment may advantageously be tailored to achieve one or more specific immune reactions, including a $CD4^+$ biased immune response, a $CD8^+$ biased immune response, antibody biased immune response, and/or a stimulated immune response (e.g., reducing checkpoint inhibition and/or by activation of immune competent cells using cytokines). Most typically, such effects are in achieved in the context of the neoepitopes originating from the recombinant nucleic acid.

Neoepitopes can be characterized as expressed random mutations in tumor cells that created unique and tumor specific antigens. Therefore, viewed from a different perspective, neoepitopes may be identified by considering the type (e.g., deletion, insertion, transversion, transition, translocation) and impact of the mutation (e.g., non-sense, missense, frame shift, etc.), which may as such serve as a content filter through which silent and other non-relevant (e.g., non-expressed) mutations are eliminated. It should also be appreciated that neoepitope sequences can be defined as sequence stretches with relatively short length (e.g., 8-12 mers or 14-20 mers) wherein such stretches will include the change(s) in the amino acid sequences. Most typically, but not necessarily, the changed amino acid will be at or near the central amino acid position. For example, a typical neoepitope may have the structure of $A_4$-N-$A_4$, or $A_3$-N-$A_5$, or $A_2$-N-$A_7$, or $A_5$-N-$A_3$, or $A_7$-N-$A_2$, where A is a proteinogenic wild type or normal (i.e., from corresponding healthy tissue of the same patient) amino acid and N is a changed amino acid (relative to wild type or relative to matched normal). Therefore, the neoepitope sequences contemplated herein include sequence stretches with relatively short length (e.g., 5-30 mers, more typically 8-12 mers, or 14-20 mers) wherein such stretches include the change(s) in the amino acid sequences. Where desired, additional amino acids may be placed upstream or downstream of the changed amino acid, for example, to allow for additional antigen processing in the various compartments (e.g., for proteasome processing in the cytosol, or specific protease processing in the endosomal and/or lysosomal compartments) of a cell.

Thus, it should be appreciated that a single amino acid change may be presented in numerous neoepitope sequences that include the changed amino acid, depending on the position of the changed amino acid. Advantageously, such sequence variability allows for multiple choices of neoepitopes and as such increases the number of potentially useful targets that can then be selected on the basis of one or more desirable traits (e.g., highest affinity to a patient HLA-type, highest structural stability, etc.). Most typically, neoepitopes will be calculated to have a length of between 2-50 amino acids, more typically between 5-30 amino acids, and most typically between 8-12 amino acids, or 14-20 amino acids, with the changed amino acid preferably centrally located or otherwise situated in a manner that improves its binding to MHC. For example, where the epitope is to be presented by the MHC-I complex, a typical neoepitope length will be about 8-12 amino acids, while the typical neoepitope length for presentation via MHC-II complex will have a length of about 14-20 amino acids. As will be readily appreciated, since the position of the changed amino acid in the neoepitope may be other than central, the actual peptide sequence and with that actual topology of the neoepitope may vary considerably, and the neoepitope sequence with a desired binding affinity to the MHC-I or MHC-II presentation and/or desired protease processing will typically dictate the particular sequence.

Of course, it should be appreciated that the identification or discovery of neoepitopes may start with a variety of biological materials, including fresh biopsies, frozen, or otherwise preserved tissue or cell samples, circulating tumor cells, exosomes, various body fluids (and especially blood), etc. Therefore, suitable methods of omics analysis include nucleic acid sequencing, and particularly NGS methods operating on DNA (e.g., Illumina sequencing, ion torrent sequencing, 454 pyrosequencing, nanopore sequencing, etc.), RNA sequencing (e.g., RNAseq, reverse transcription based sequencing, etc.), and in some cases protein sequencing or mass spectroscopy based sequencing (e.g., SRM, MRM, CRM, etc.).

As such, and particularly for nucleic acid based sequencing, it should be particularly recognized that high-throughput genome sequencing of a tumor tissue will allow for rapid identification of neoepitopes. However, it must be appreciated that where the so obtained sequence information is compared against a standard reference, the normally occurring inter-patient variation (e.g., due to SNPs, short indels, different number of repeats, etc.) as well as heterozygosity will result in a relatively large number of potential false positive neoepitopes. Notably, such inaccuracies can be eliminated where a tumor sample of a patient is compared against a matched normal (i.e., non-tumor) sample of the same patient.

In one especially preferred aspect of the inventive subject matter, DNA analysis is performed by whole genome sequencing and/or exome sequencing (typically at a coverage depth of at least 10×, more typically at least 20×) of both tumor and matched normal sample. Alternatively, DNA data may also be provided from an already established sequence record (e.g., SAM, BAM, FASTA, FASTQ, or VCF file) from a prior sequence determination of the same patient. Therefore, data sets suitable for use herein include unprocessed or processed data sets, and exemplary preferred data sets include those having BAM format, SAM format, GAR format, FASTQ format, or FASTA format, as well as BAM-BAM, SAMBAM, and VCF data sets. However, it is especially preferred that the data sets are provided in BAM format or as BAMBAM diff objects as is described in US2012/0059670A1 and US2012/0066001A1. Moreover, it should be noted that the data sets are reflective of a tumor and a matched normal sample of the same patient. Thus, genetic germ line alterations not giving rise to the tumor (e.g., silent mutation, SNP, etc.) can be excluded. Of course, it should be recognized that the tumor sample may be from an initial tumor, from the tumor upon start of treatment, from a recurrent tumor and/or metastatic site, etc. In most cases, the matched normal sample of the patient is blood, or a non-diseased tissue from the same tissue type as the tumor. The computational analysis of the sequence data may be performed in numerous manners. In most preferred methods, however, analysis is performed in silico by location-guided synchronous alignment of tumor and normal samples as, for example, disclosed in US 2012/0059670 and US 2012/0066001 using BAM files and BAM servers. Such analysis advantageously reduces false positive neoepitopes and significantly reduces demands on memory and computational resources.

It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

Viewed from a different perspective, a patient- and cancer-specific in silico collection of sequences can be established that encode neoepitopes having a predetermined length of, for example, between 5 and 25 amino acids and include at least one changed amino acid. Such collection will typically include for each changed amino acid at least two, at least three, at least four, at least five, or at least six members in which the position of the changed amino acid is not identical. Such collection advantageously increases potential candidate molecules suitable for immune therapy and can then be used for further filtering (e.g., by subcellular location, transcription/expression level, MHC-I and/or II affinity, etc.) as is described in more detail below.

For example, and using synchronous location guided analysis to tumor and matched normal sequence data, the inventors previously identified various cancer neoepitopes from a variety of cancers and patients, including the following cancer types: BLCA, BRCA, CESC, COAD, DLBC, GBM, HNSC, KICH, KIRC, KIRP, LAML, LGG, LIHC, LUAD, LUSC, OV, PRAD, READ, SARC, SKCM, STAD, THCA, and UCEC. Exemplary neoepitope data for these cancers can be found in International application PCT/US16/29244, incorporated by reference herein.

Depending on the type and stage of the cancer, as well as the patient's immune status it should be recognized that not all of the identified neoepitopes will necessarily lead to a therapeutically equally effective reaction in a patient. Indeed, it is well known in the art that only a fraction of neoepitopes will generate an immune response. To increase likelihood of a therapeutically desirable response, the initially identified neoepitopes can be further filtered. Of course, it should be appreciated that downstream analysis need not take into account silent mutations for the purpose of the methods presented herein. However, preferred mutation analyses will provide in addition to the particular type of mutation (e.g., deletion, insertion, transversion, transition, translocation) also information of the impact of the mutation (e.g., non-sense, missense, etc.) and may as such serve as a first content filter through which silent mutations are eliminated. For example, neoepitopes can be selected for further consideration where the mutation is a frame-shift, non-sense, and/or missense mutation. In a further filtering approach, neoepitopes may also be subject to detailed analysis for sub-cellular location parameters. For example, neoepitope sequences may be selected for further consideration if the neoepitopes are identified as having a membrane associated location (e.g., are located at the outside of a cell membrane of a cell) and/or if an in silico structural calculation confirms that the neoepitope is likely to be solvent exposed, or presents a structurally stable epitope (e.g., *J Exp Med* 2014), etc.

With respect to filtering neoepitopes, it is generally contemplated that neoepitopes are especially suitable for use herein where omics (or other) analysis reveals that the neoepitope is actually expressed. Identification of expression and expression level of a neoepitope can be performed in all manners known in the art and preferred methods include quantitative RNA (hnRNA or mRNA) analysis and/or quantitative proteomics analysis. Most typically, the threshold level for inclusion of neoepitopes will be an expression level of at least 20%, at least 30%, at least 40%, or at least 50% of expression level of the corresponding matched normal sequence, thus ensuring that the (neo) epitope is at least potentially 'visible' to the immune system. Consequently, it is generally preferred that the omics analysis also includes an analysis of gene expression (transcriptomic analysis) to so help identify the level of expression for the gene with a mutation.

In yet another aspect of filtering, the neoepitopes may be compared against a database that contains known human sequences (e.g., of the patient or a collection of patients) to so avoid use of a human-identical sequence. Moreover, filtering may also include removal of neoepitope sequences that are due to SNPs in the patient where the SNPs are present in both the tumor and the matched normal sequence. For example, dbSNP (The Single Nucleotide Polymorphism Database) is a free public archive for genetic variation within and across different species developed and hosted by the National Center for Biotechnology Information (NCBI) in collaboration with the National Human *Genome Research* Institute (NHGRI). Although the name of the database implies a collection of one class of polymorphisms only (single nucleotide polymorphisms (SNPs)), it in fact contains a relatively wide range of molecular variation: (1) SNPs, (2) short deletion and insertion polymorphisms (indels/DIPs), (3) microsatellite markers or short tandem repeats (STRs), (4) multinucleotide polymorphisms (MNPs), (5) heterozygous sequences, and (6) named variants. The dbSNP accepts apparently neutral polymorphisms, polymorphisms corresponding to known phenotypes, and regions of no variation. Using such database and other filtering options as described above, the patient and tumor specific neoepitopes may be filtered to remove those known sequences, yielding a sequence set with a plurality of neoepitope sequences having substantially reduced false positives.

Nevertheless, despite filtering, it should be recognized that not all neoepitopes will be visible to the immune system as the neoepitopes also need to be processed where present in a larger context (e.g., within a polytope) and presented on the MHC complex of the patient. In that context, it must be appreciated that only a fraction of all neoepitopes will have sufficient affinity for presentation. Consequently, and especially in the context of immune therapy it should be apparent that neoepitopes will be more likely effective where the neoepitopes are properly processed, bound to, and presented by the MHC complexes. Viewed from another perspective, treatment success will be increased with an increasing number of neoepitopes that can be presented via the MHC complex, wherein such neoepitopes have a minimum affinity to the patient's HLA-type. Consequently, it should be appreciated that effective binding and presentation is a combined function of the sequence of the neoepitope and the particular HLA-type of a patient. Therefore, HLA-type determination of the patient tissue is typically required. Most typically, the HLA-type determination includes at least three MHC-I sub-types (e.g., HLA-A, HLA-B, HLA-C) and at least three MHC-II sub-types (e.g., HLA-DP, HLA-DQ, HLA-DR), preferably with each subtype being determined to at least 2-digit or at least 4-digit depth. However, greater depth (e.g., 6 digit, 8 digit) is also contemplated.

HLA determination can be performed using various methods in wet-chemistry that are well known in the art, and all of these methods are deemed suitable for use herein. However, in especially preferred methods, the HLA-type can also be predicted from omics data in silico using a reference sequence containing most or all of the known and/or common HLA-types. One particularly suitable method of in silico determination of the HLA-type is described in WO 2017/035392.

Once the HLA-type of the patient is ascertained (using known chemistry or in silico determination), a structural solution for the HLA-type is calculated and/or obtained from a database, which is then used in a docking model in silico to determine binding affinity of the (typically filtered) neoepitope to the HLA structural solution. For example, suitable systems for determination of binding affinities include the NetMHC platform (see e.g., *Nucleic Acids Res.* 2008 Jul. 1; 36(Web Server issue): W509-W512.). Neoepitopes with high affinity (e.g., less than 100 nM, less than 75 nM, less than 50 nM) for a previously determined HLA-type are then selected for vaccine creation, along with the knowledge of the patient's MHC-I/II subtype.

Of course, it should be appreciated that matching of the patient's HLA-type to the patient- and cancer-specific neoepitope can be done using systems other than NetMHC, and suitable systems include NetMHC II, NetMHCpan, IEDB Analysis Resource (URL immuneepitope.org), RankPep, PREDEP, SVMHC, Epipredict, HLABinding, and others (see e.g., *J Immunol Methods* 2011; 374:1-4). In calculating the highest affinity, it should be noted that the collection of neoepitope sequences in which the position of the altered amino acid is moved (supra) can be used. Alternatively, or additionally, modifications to the neoepitopes may be implemented by adding N- and/or C-terminal modifications to further increase binding of the expressed neoepitope to the patient's HLA-type. Thus, neoepitopes may be native as identified or further modified to better match a particular HLA-type. Moreover, where desired, binding of corresponding wild type sequences (i.e., neoepitope sequence without amino acid change) can be calculated to ensure high differential affinities. For example, especially preferred high differential affinities in MHC binding between the neoepitope and its corresponding wild type sequence are at least 2-fold, at least 5-fold, at least 10-fold, at least 100-fold, at least 500-fold, at least 1000-fold, etc.).

Upon identification of desired neoepitopes, one or more immune therapeutic agents may be prepared using the sequence information of the neoepitope. Among other agents, it is especially preferred that the patient may be treated with a virus that is genetically modified with a nucleic acid construct as further discussed below that leads to expression of at least one of the identified neoepitopes to initiate an immune response against the tumor. For example, suitable viruses include adenoviruses, adeno-associated viruses, alphaviruses, herpes viruses, lentiviruses, etc. However, adenoviruses are particularly preferred. Moreover, it is further preferred that the virus is a replication deficient and non-immunogenic virus, which is typically accomplished by targeted deletion of selected viral proteins (e.g., E1, E3 proteins). Such desirable properties may be further enhanced by deleting E2b gene function, and high titers of recombinant viruses can be achieved using genetically modified human 293 cells as has been recently reported (e.g., *J Virol.* 1998 February; 72(2): 926-933).

Regardless of the type of recombinant virus it is contemplated that the virus may be used to infect patient (or non-patient) cells ex vivo or in vivo. For example, the virus may be injected subcutaneously or intravenously, or may be injected into the tumor to so infect the patient's cells, and especially antigen presenting cells. Alternatively, immune competent cells (e.g., NK cells, T cells, macrophages, dendritic cells, etc.) of the patient (or from an allogeneic source) may be infected in vitro and then transfused to the patient. Alternatively, immune therapy need not rely on a virus but may be effected with nucleic acid transfection or vaccination using RNA or DNA, or other recombinant vector that leads to the expression of the neoepitopes (e.g., as single peptides, tandem mini-gene, etc.) in desired cells, and especially antigen presenting cells (e.g., dendritic cells).

Most typically, the desired nucleic acid sequences (for expression from virus infected cells) are under the control of appropriate regulatory elements well known in the art. For example, suitable promoter elements include constitutive strong promoters (e.g., SV40, CMV, UBC, EF1A, PGK, CAGG promoter), but inducible promoters are also deemed suitable for use herein, particularly where induction conditions are typical for a tumor microenvironment. For example, inducible promoters include those sensitive to hypoxia and promoters that are sensitive to TGF-β or IL-8 (e.g., via TRAF, JNK, Erk, or other responsive elements promoter). In other examples, suitable inducible promoters include the tetracycline-inducible promoter, the myxovirus resistance 1 (Mxl) promoter, etc.

In this context, it should be appreciated that the inventors have discovered that the manner of neoepitope arrangement and rational-designed trafficking of the neoepitopes can have a substantial impact on the efficacy of various immune therapeutic compositions. For example, single neoepitopes can be expressed individually from the respective recombinant constructs that are delivered as a single plasmid, viral expression construct, etc. Alternatively, multiple neoepitopes can be separately expressed from individual promoters t form individual mRNA that are then individually translated into the respective neoepitopes, or from a single mRNA comprising individual translation starting points for each neoepitope sequence (e.g., using 2A or IRES signals). Notably, while such arrangements are generally thought to allow for controlled delivery of proper neoepitope peptide, efficacy of such expression systems has been less than desirable (data not shown).

In contrast, where multiple neoepitopes were expressed from a single transcript to so form a single transcript that is then translated into a single polytope (i.e., polypeptide with a series of concatemerically linked neoepitopes, optionally with intervening linker sequences) expression, processing, and antigen presentation was found to be effective. Notably, the expression of polytopes requires processing by the appropriate proteases (e.g., proteasome, endosomal proteases, lysosomal proteases) within a cell to yield the neoepitope sequences, and polytopes led to improved antigen processing and presentation for most neoepitopes as compared to expression of individual neoepitopes, particularly where the individual neoepitopes had a relatively short length (e.g., less than 25 amino acids; results not shown). Moreover, such approach also allows rational design of protease sensitive sequence motifs between the neoepitope peptide sequences to so assure or avoid processing by specific proteases as the proteasome, endosomal proteases, and lysosomal proteases have distinct cleavage preferences. Therefore, polytopes may be designed that include not only linker sequences to spatially separate neoepitopes, but also sequence portions (e.g., between 3-15 amino acids) that will be preferentially cleaved by a specific protease.

With respect to the total number of neoepitope sequences in a polytope it is generally preferred that the polytope comprise at least two, or at least three, or at least five, or at least eight, or at least ten neoepitope sequences. Indeed, the payload capacity of the recombinant DNA is generally contemplated the limiting factor, along with the availability of filtered and appropriate neoepitopes. Therefore, adenoviral expression vectors, and particularly Adv5 are especially preferred as such vectors can accommodate up to 14 kb in recombinant payload.

In still further contemplated aspects of the inventive subject matter, it should be noted that the neoepitopes/polytopes can be directed towards a specific sub-cellular compartment (e.g., cytosol, endosome, lysosome), and with that, towards a particular MHC presentation type. Such directed expression, processing, and presentation is particularly advantageous as contemplated compositions may be prepared that direct an immune response towards a $CD8^+$ type response (where the polytope is directed to the cytoplasmic space) or towards a $CD4^+$ type response (where the polytope is directed to the endosomal/lysosomal compartment). Moreover, it should be recognized that polytopes that would ordinarily be presented via the MHC-I pathway can be presented via the MHC-II pathway (and thereby mimick cross-presentation of neoepitopes). Therefore, it should be appreciated that neoepitope and polytope sequences may be designed and directed to one or both MHC presentation pathways using suitable sequence elements. With respect to routing the so expressed neoepitopes to the desired MHC-system, it is noted that the MHC-I presented peptides will typically arise from the cytoplasm via proteasome processing and delivery through the endoplasmatic reticulum. Thus, expression of the epitopes intended for MHC-I presentation will generally be directed to the cytoplasm as is further discussed in more detail below. On the other hand, MHC-II presented peptides will typically arise from the endosomal and lysosomal compartment via degradation and processing by acidic proteases (e.g., legumain, cathepsin L and cathepsin S) prior to delivery to the cell membrane.

Moreover, it is contemplated that proteolytic degradation of the polytope can also be enhanced using various methods, and especially contemplated methods include addition of a cleavable or non-cleavable ubiquitin moiety to the N-terminus, and/or placement of one or more destabilizing amino acids (e.g., N, K, C, F, E, R, Q) to the N-terminus of the polytope where the presentation is directed towards MHC-I.

On the other hand, where presentation is directed towards MHC-II, cleavage sites for particular endosomal or lysosomal proteases can be engineered into the polytope to so facilitate of promote antigen processing.

Therefore, in contemplated aspects of the inventive subject matter, signal and/or leader peptides may be used for trafficking neoepitopes and/or polytopes to the endosomal and lysosomal compartment, or for retention in the cytoplasmic space. For example, where the polytope is to be exported to the endosomal and lysosomal compartment, a leader peptide such as the CD1b leader peptide may be employed to sequester the (nascent) protein from the cytoplasm. Additionally, or alternatively, targeting presequences and/or targeting peptides can be employed. The presequences of the targeting peptide may be added to the N-terminus and/or C-terminus and typically comprise between 6-136 basic and hydrophobic amino acids. In case of peroxisomal targeting, the targeting sequence may be at the C-terminus. Other signals (e.g., signal patches) may be used and include sequence elements that are separate in the peptide sequence and become functional upon proper peptide folding. In addition, protein modifications like glycosylations can induce targeting. Among other suitable targeting signals, the inventors contemplate peroxisome targeting signal 1 (PTS1), a C-terminal tripeptide, and peroxisome targeting signal 2 (PTS2), which is a nonapeptide located near the N-terminus. In still further aspects, endosomal compartments can also be targeted using human CD1 tail sequences (see e.g., Immunology, 122, 522-531). For example, lysosomal targeting can be achieved using a LAMP1-TM (transmembrane) sequence, while recycling endosomes can be targeted via the CD1a tail targeting sequence, and sorting endosomes can be targeted via the CD1c tail targeting sequence as is shown in more detail further below.

With respect to co-stimulatory ligands and their receptors, it is generally contemplated that all factors that form part of the immune synapse are deemed suitable for use herein. Thus, and among other factors, preferred ligands and receptors include Ox40, Ox40 ligand, 4-1BB, 4-1BB ligand, GitR, GitR ligand, CTLA4, CTLA-4, B7.1, B7.2, CD154, and CD40, and all known isoforms thereof. It should be noted that OX40 ligand co-stimulates T-cell proliferation and cytokine production in conjunction with OX40, which is a costimulatory molecule implicated in long-term T-cell immunity. Likewise, 4-1BB is the receptor for TNFSF9/4-1BBL, which is active during T cell activation. Notably, 4-1BB induces the proliferation of activated peripheral blood T-cells, and may also play a role in cognate interactions between T-cells and B-cells/macrophages. CTLA4, CTLA-4, B7.1, B7.2 are known early co-stimulatory factors that participate in immune synapse formation, while CD40 and its ligand CD154 costimulate T-cell proliferation and cytokine production. Furthermore, CD40/CD154 interaction on T-cells generate a costimulatory signal which enhances the production of IL4 and IL10 in conjunction with the TCR/CD3 ligation and CD28 co-stimulation (PubMed: 8617933). CD40/CD154 interaction also induces the activation of NF-kappa-B and kinases MAPK8 and PAK2 in T-cells.

Typically, preferred ligand and receptor sequences are human sequences (or humanized where the source is non-human such as murine, porcine, etc.), and all of these sequences are known in the art. For example, a suitable Ox40 ligand protein sequence is known from UniProt P23510, is known from UniProt P43489, 4-1BB is known from UniProtKB Q07011, 4-1BB ligand is known from UniProt P41273, GitR is known from UniProtKB Q9Y5U5, GitR ligand is known from UniProtKB Q9UNG2, CTLA4 is known from UniProtKB P16410, CTLA-4 ligand is known from UniProtKB P42081, B7.1 is known from UniProtKB P33681, B7.2 is known from UniProtKB P42081, CD154 is known from UniProtKB P29965, and CD40 is known from UniProtKB P25942.

It should be appreciated that the expression of the co-stimulatory receptor and its ligand may be achieved via an at least bicistronic arrangement with an intervening IRES sequence, or expression of the receptor and the ligand gene can be driven from separate promoter elements. In still further contemplated aspects the expression may also be from a polypeptide with an intervening self-cleaving sequence. Moreover, it should be noted that where antigen presenting cells are transfected (e.g., using an adenoviral expression system), expression of at least one of the ICOS ligand, B7.1, B7.2, CD40, 4-1BB ligand, OX40 ligand, and/or GitR ligand will be in form of the native protein. As such, these proteins will be expressed with a transmembrane domain that ensures proper anchoring and presentation of the ligand to the naïve T cell. Thus, both the ligand and the receptor (e.g., OX40 ligand and OX40 receptor, or 4-1BB ligand and 4-1BB receptor) will be present on the cell membrane in the antigen presenting cell.

On the other hand, the corresponding receptor proteins may (but do not need) be truncated such that the transmembrane domain is removed from the receptor sequence to facilitate formation of a soluble receptor that can then bind to the ligand. Moreover, in such case it is typically preferred that the corresponding receptor protein will include a signal sequence that facilitates secretion of the protein. For example, the SPARC leader sequence may be added to a neoepitope or polytope sequence, leading to in vivo secretion of the neoepitope or polytope sequence into the extracellular space. Therefore, using an unmodified ligand and a modified receptor, it is contemplated that the antigen presenting cell will present the ligand and the modified receptor bound to the ligand in the context of an immune synapse.

Alternatively, it is contemplated that the ligand and the receptor (e.g., OX40 ligand and OX40 receptor, or 4-1BB ligand and 4-1BB receptor) may be coupled together as a fusion protein such that the ligand is anchored in the cell membrane using its native transmembrane domain and that the receptor is exposed to the outside of the cell towards a T cell. Most typically, the fusion protein will use a linker portion (typically a flexible linker with between 2-60 amino acids) to allow coupling of the ligand to the receptor in a sterically appropriate manner. In other aspects, no linker between the ligand and the receptor is required and receptor-ligand interaction and binding is driven by affinity. In such case, it is generally preferred that receptor will include a leader sequence for secretion.

Regardless of the manner of co-expression, it should be appreciated that the presence of both the co-stimulatory ligand (which is typically present on the antigen presenting cell) and the corresponding receptor will further enhance the strength and duration of an immune synapse between the antigen presenting cell and a naïve T cell such that the T cell will mature into an activated cytotoxic T cell. Such strengthening may be due, in part, to a larger quantity of ligands on the antigen presenting cell, due to protein/protein interactions between the co-expressed receptor and the ligands leading to stimulation of the antigen presenting cells by the ligands and concomitant stimulation of the T cell, and/or due to protein/protein interactions between the co-expressed receptor on the dendritic cell and other receptors and proteins on the T cell. Therefore, it should be recognized that a strong immune synapse may form between the antigen presenting cell and the T cells in the context of the co-expressed antigens/neoepitopes, which will lead to a stimulatory response in the T cell. Consequently, recombinant nucleic acid constructs and viruses are contemplated that comprise a nucleic acid sequence encoding one or more polytopes that are directed towards MHC I and/or MHC II, and that further include at least one ligand/receptor pair of a co-stimulatory complex (e.g., OX40 ligand and OX40 receptor, or 4-1BB ligand and 4-1BB receptor). Of course, as already noted above and shown in FIG. 2, additional components may further be present in the recombinant nucleic acid constructs or virus, and an especially preferred additional component is a chimeric protein that includes a chimeric molecule that has a targeting portion and a chemokine portion, wherein the targeting portion preferably binds to a component of a necrotic cell as is described in more detail below.

For example, especially preferred chimeric molecule with a targeting portion and a chemokine portion include those in which the targeting portion binds to a histone, nucleolin, or a ssDNA of a necrotic cell or a neoepitope of a tumor cell, and in which the chemokine portion comprises a chemokine that is effective to attract at least one of a dendritic cell, a macrophage, a T cell, and a NK cell. For example, suitable chemokines especially include an inflammatory chemokine or portion thereof (e.g., LEC, CCL1, CCL2, CCL3, CCL4, CCL5, CCL11, CCL17, CCL22, CXCL-8, CXCL-10, and CXCL-14).

Most typically, the targeting portion will be a portion of an antibody with desired binding specificity, or a truncated version thereof. Therefore, an especially preferred chimeric molecule will have a scFv portion that has affinity towards a component of a necrotic cell and a chemokine portion. For example, antibodies with such binding specificity are known in the art, and all of these antibody sequences (and the especially CDR regions of the light and heavy chains in these sequences) are deemed suitable for use herein. Among other sequences, particularly preferred antibodies include TNT-1, TNT-2, TNT-3, and NHS76 as described in U.S. Pat. No. 8,795,672. Of course, it should be appreciated that where the chimeric protein is not a full-length antibody, binding specificity may be maintained by truncating the antibody or by CDR grafting into a suitable framework. Consequently, humanized antibody portions, Fab, scFv, F(ab)$_2$, and Fab' are expressly contemplated herein. In addition, it should be noted that suitable binding portions may also generated as synthetic antibodies against a patient's neoepitopes as is described in WO 2016/172722.

Fusion proteins between the antibody and the chemokine can be prepared in numerous manners, and an exemplary suitable manner of fusion protein production between an antibody and a chemokine is described in U.S. Pat. No. 8,795,672. Likewise, where the binding portion is an scFv, the fusion may be performed as described elsewhere (e.g., *Biotechnol Appl Biochem.* 2006 November; 45(Pt 3):147-54) or include a linker portion (typically a flexible linker G/S linker or A$_n$ linker, having between 5 and 50 amino acids) to couple the chemokine to the binding portion.

Regardless of the manner of production of the chimeric protein, it should be appreciated that such construct will in the context of tumor antigen/neoepitope expression (preferably while co-expressing co-stimulatory ligands and receptors) provide a further signal in the tumor microenvironment that attracts antigen presenting cells (and especially dendritic cells), T cells, and NK cells, all of which will further enhance and complement T cell activation in the context of the patients tumor relevant antigens/neoepitopes. More particularly, where necrotic tumor cells have been 'tagged' with a chimeric protein as described above, dendritic cells and T cells will enrich in the tumor microenvironment. Infection of dendritic cells with the recombinant virus will therefore result in an immune synapse formation between the T cells and the dendritic cells in the tumor in the context of the neoepitopes. In addition, the NK cells recruited to the tumor microenvironment will exert cytotoxic effects on tumor cells and naïve T cells and dendritic cells present in the microenvironment are exposed to additional antigens from tumor cells that are lysed by the NK cells.

Additionally, it is contemplated that the expression construct (e.g., recombinant viral expression vector or plasmid) may further encode further stimulatory molecules with less defined (or understood) mechanism of action such as TIM-3, TIM-4, CD48, CD58, TL1A, ICAM-1, LFA3, and members of the SLAM family. In addition to co-stimulatory molecules, the inventors also contemplate that one or more cytokines or cytokine analogs may be expressed from the recombinant nucleic acid, and especially preferred cytokines and cytokine analogs include IL-2, IL-15, and IL-a5 super-agonist (ALT-803). Moreover, it should be appreciated that expression of the co-stimulatory molecules and/or cytokines will preferably be coordinated such that the neoepitopes or polytope are expressed contemporaneously with one or more co-stimulatory molecules and/or cytokines. Thus, it is typically contemplated that the co-stimulatory molecules and/or cytokines are produced from a single transcript (which may or may not include the sequence portion encoding the polytope), for example, using an internal ribosome entry site or 2A sequence, or from multiple transcripts.

Likewise, and as discussed above, it is contemplated that the viral vector may also include a sequence portion that encodes one or more peptide ligands that bind to a checkpoint receptor. Most typically, binding will inhibit or at least reduce signaling via the receptor, and particularly contemplated receptors include CTLA-4 (especially for $CD8^+$ cells), PD-1 (especially for $CD4^+$ cells), TIM1 receptor, 2B4, and CD160. For example, suitable peptide binders can include antibody fragments and especially scFv, but also small molecule peptide ligands (e.g., isolated via RNA display or phage panning) that specifically bind to the receptors. Once more, it should be appreciated that expression of the peptide molecules will preferably be coordinated such that the neoepitopes or polytope are expressed contemporaneously with one or more of the peptide ligands. Thus, it is typically contemplated that the peptide ligands are produced from a single transcript (which may or may not include the sequence portion encoding the polytope), for example, using an internal ribosome entry site or 2A sequence, or from multiple transcripts.

It should be appreciated that all of the above noted co-stimulatory genes and genes coding for inhibitory proteins that interfere with/down-regulate checkpoint inhibition are well known in the art, and sequence information of these genes, isoforms, and variants can be retrieved from various public resources, including sequence data bases accessible at the NCBI, EMBL, GenBank, RefSeq, etc. Moreover, while the above exemplary stimulating molecules are preferably expressed in full length form as expressed in human, modified and non-human forms are also deemed suitable so long as such forms assist in stimulating or activating T-cells. Therefore, muteins, truncated forms and chimeric forms are expressly contemplated herein.

Where the expression construct is a viral expression construct (e.g., an adenovirus, and especially AdV with E1 and E2b deleted), it is contemplated that the recombinant viruses may then be individually or in combination used as a therapeutic vaccine in a pharmaceutical composition, typically formulated as a sterile injectable composition with a virus titer of between $10^6$-$10^{13}$ virus particles, and more typically between $10^9$-$10^{12}$ virus particles per dosage unit. Alternatively, virus may be employed to infect patient (or other HLA matched) cells ex vivo and the so infected cells are then transfused to the patient. In further examples, treatment of patients with the virus may be accompanied by allografted or autologous natural killer cells or T cells in a bare form or bearing chimeric antigen receptors expressing antibodies targeting neoepitope, neoepitopes, tumor associated antigens or the same payload as the virus. The natural killer cells, which include the patient-derived NK-92 cell line, may also express CD16 and can be coupled with an antibody.

Where desired, additional therapeutic modalities may be employed which may be neoepitope based (e.g., synthetic antibodies against neoepitopes as described in WO 2016/172722), alone or in combination with autologous or allogenic NK cells, and especially haNK cells or taNK cells (e.g., both commercially available from NantKwest, 9920 Jefferson Blvd. Culver City, Calif. 90232). Where haNK or taNK cells are employed, it is particularly preferred that the haNK cell carries a recombinant antibody on the CD16 variant that binds to a neoepitope of the treated patient, and where taNK cells are employed it is preferred that the chimeric antigen receptor of the taNK cell binds to a neoepitope of the treated patient. The additional treatment modality may also be independent of neoepitopes, and especially preferred modalities include cell-based therapeutics such as activated NK cells (e.g., aNK cells, commercially available from NantKwest, 9920 Jefferson Blvd. Culver City, Calif. 90232), and non cell-based therapeutics such as chemotherapy and/or radiation. In still further contemplated aspects, immune stimulatory cytokines, and especially IL-2, IL15, and IL-21 may be administered, alone or in combination with one or more checkpoint inhibitors (e.g., ipilimumab, nivolumab, etc.). Similarly, it is still further contemplated that additional pharmaceutical intervention may include administration of one or more drugs that inhibit immune suppressive cells, and especially MDSCs Tregs, and M2 macrophages. Thus, suitable drugs include IL-8 or interferon-γ inhibitors or antibodies binding IL-8 or interferon-γ, as well as drugs that deactivate MDSCs (e.g., NO inhibitors, arginase inhibitors, ROS inhibitors), that block development of or differentiation of cells to MDSCs (e.g., IL-12, VEGF-inhibitors, bisphosphonates), or agents that are toxic to MDSCs (e.g., gemcitabine, cisplatin, 5-FU). Likewise, drugs like cyclophosphamide, daclizumab, and anti-GITR or anti-OX40 antibodies may be used to inhibit Tregs.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). Most preferably, the recombinant virus is administered via subcutaneous or subdermal injection. However, in other contemplated aspects, administration may also be intravenous injection. Alternatively, or additionally, antigen presenting cells may be isolated or grown from cells of the patient, infected in vitro, and then transfused to the patient. Therefore, it should be appreciated that contemplated systems and methods can be considered a complete drug discovery system (e.g., drug discovery, treatment protocol, validation, etc.) for highly personalized cancer treatment.

To trigger overexpression or transcription of stress signals, it is also contemplated that the chemotherapy and/or radiation for the patient may be done using a low-dose regimen, preferably in a metronomic fashion. For example, it is generally preferred that such treatment will use doses effective to affect at least one of protein expression, cell division, and cell cycle, preferably to induce apoptosis or at least to induce or increase the expression of stress-related genes (and particularly NKG2D ligands). Thus, in further contemplated aspects, such treatment will include low dose treatment using one or more chemotherapeutic agents. Most typically, low dose treatments will be at exposures that are equal or less than 70%, equal or less than 50%, equal or less than 40%, equal or less than 30%, equal or less than 20%, equal or less than 10%, or equal or less than 5% of the $LD_{50}$ or $IC_{50}$ for the chemotherapeutic agent. Additionally, where advantageous, such low-dose regimen may be performed in a metronomic manner as described, for example, in U.S. Pat. Nos. 7,758,891, 7,771,751, 7,780,984, 7,981,445, and 8,034,375.

With respect to the particular drug used in such low-dose regimen, it is contemplated that all chemotherapeutic agents are deemed suitable. Among other suitable drugs, kinase inhibitors, receptor agonists and antagonists, anti-metabolic, cytostatic and cytotoxic drugs are all contemplated herein. However, particularly preferred agents include those identified to interfere or inhibit a component of a pathway that drives growth or development of the tumor. Suitable drugs can be identified using pathway analysis on omics data as described in, for example, WO 2011/139345 and WO 2013/062505. Most notably, so achieved expression of stress-related genes in the tumor cells will result in surface presentation of NKG2D, NKP30, NKP44, and/or NKP46 ligands, which in turn activate NK cells to specifically destroy the tumor cells. Thus, it should be appreciated that low-dose chemotherapy may be employed as a trigger in tumor cells to express and display stress related proteins, which in turn will trigger NK-cell activation and/or NK-cell mediated tumor cell killing. Additionally, NK-cell mediated killing will be associated with release of intracellular tumor specific antigens, which is thought to further enhance the immune response.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Where the specification claims refers to at least one of something selected from the group consisting of A, B, C . . . and N, the text should be interpreted as requiring only one element from the group, not A plus N, or B plus N, etc.

What is claimed is:

1. A method of activating T-cells in a cancer patient to generate memory T-cells, the method comprising:
using tumor omics data and matched normal omics data obtained from a tumor sample from the patient and a matched normal sample to generate in silico a plurality of neoepitopes that contain at least one patient- and cancer-specific neoepitope, wherein the omics data from each of the tumor and the matched normal sample include data selected from the group consisting of whole genomic sequencing data, exome sequencing data, transcriptome data, and combinations thereof;
filtering in silico the plurality of neoepitopes to so obtain a subset of filtered neoepitopes wherein the filtering is filtering by type of mutation, filtering by strength of expression, filtering by subcellular location, and/or filtering by binding affinity towards an HLA-type of the patient;
genetically modifying an antigen presenting cell (APC) by infecting the APC with a recombinant virus that comprises a single nucleic acid strand encoding a means for checkpoint inhibition, a co-stimulatory ligand/receptor pair, a MHC-I polytope, and a MHC-II polytope; wherein the MHC-I polytope and the MHC-II polytope each comprise a plurality of the filtered neoepitopes;
expressing, in the genetically modified APC, the means for checkpoint inhibition, the co-stimulatory ligand/receptor pair, the MHC-I polytope, and the MHC-II polytope,
wherein the means for checkpoint inhibition is an antibody,
wherein the co-stimulatory ligand/receptor pair is 4-1BBL/4-1BB,
wherein the ligand and the receptor of the ligand/receptor pair are coupled together via a linker to form a chimeric protein, and
wherein the MHC-I polytope and the MHC-II polytope are coupled together via a linker comprising a self-cleaving peptide; and
contacting the genetically modified APC with a naïve T-cell in the cancer patient.

2. The method of claim 1, wherein the means for checkpoint inhibition is ipilimumab or nivolumab.

3. The method of claim 1, wherein the APC is infected by administering the recombinant virus to the cancer patient to thereby treat the cancer.

4. The method of claim 1, wherein the recombinant virus further comprises a nucleotide sequence encoding a cell adhesion molecule.

5. The method of claim 1, wherein the recombinant virus further comprises a nucleotide sequence encoding a chimeric molecule that has a targeting portion and a chemokine portion, wherein the targeting portion binds to a component of a necrotic cell.

6. The method of claim 1, wherein the step of infecting is performed in vivo.

* * * * *